(12) United States Patent
Donde et al.

(10) Patent No.: US 9,006,464 B2
(45) Date of Patent: Apr. 14, 2015

(54) SUBSTITUTED CYCLOPENTANES HAVING PROSTAGLANDIN ACTIVITY

(75) Inventors: Yariv Donde, Dana Point, CA (US); Jeremiah H. Nguyen, La Puente, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 1076 days.

(21) Appl. No.: 12/265,062

(22) Filed: Nov. 5, 2008

(65) Prior Publication Data

US 2009/0124676 A1    May 14, 2009

Related U.S. Application Data

(60) Provisional application No. 60/986,849, filed on Nov. 9, 2007.

(51) Int. Cl.
   *C07D 333/40*    (2006.01)
   *A61K 31/381*    (2006.01)
   *C07D 263/34*    (2006.01)

(52) U.S. Cl.
   CPC .......... *C07D 333/40* (2013.01); *C07D 263/34* (2013.01)

(58) Field of Classification Search
   USPC ............................................. 549/71; 514/448
   See application file for complete search history.

(56) References Cited

U.S. PATENT DOCUMENTS

| | | | | |
|---|---|---|---|---|
| 4,012,429 A * | 3/1977 | Sakai et al. | ................... | 560/121 |
| 5,698,598 A * | 12/1997 | Woodward | ................... | 514/530 |
| 5,877,211 A * | 3/1999 | Woodward | ................... | 514/530 |
| 7,091,231 B2 * | 8/2006 | Donde et al. | ................... | 514/381 |
| 7,585,895 B2 * | 9/2009 | Donde et al. | ................... | 514/530 |
| 2006/0205800 A1 | 9/2006 | Donde | | |
| 2007/0129552 A1 | 6/2007 | Donde | | |

FOREIGN PATENT DOCUMENTS

WO    WO 2006063179 A1 *   6/2006
WO    WO 2008/094958       8/2008

OTHER PUBLICATIONS

U.S. Appl. No. 11/553,143, filed Jun. 7, 2007, Yariv Donde.
Silverman: "Prodrugs and Drug Delivery Systems," Organic Chem. of Drug Design and Drug Action, 2nd ed., 2004, pp. 496-557.

* cited by examiner

*Primary Examiner* — David K O Dell
(74) *Attorney, Agent, or Firm* — Jonathan Y. Bass

(57) ABSTRACT

Disclosed herein are compounds having a formula:

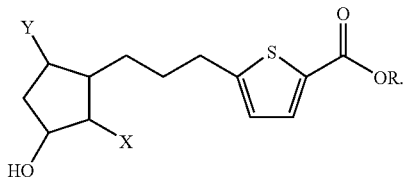

Therapeutic methods, medicaments, and compositions related thereto are also disclosed.

3 Claims, No Drawings

SUBSTITUTED CYCLOPENTANES HAVING PROSTAGLANDIN ACTIVITY

CROSS REFERENCE TO RELATED APPLICATIONS

This application is based on, and claims the benefit of, U.S. Provisional Application No. 60/986,849, filed Nov. 9, 2007 entitled "SUBSTITUTED CYCLOPENTANES HAVING PROSTAGLANDIN ACTIVITY", and which is incorporated herein by reference.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

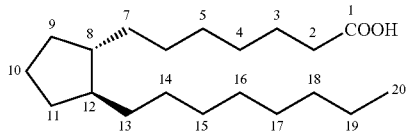 [SMILES: CCCCCCCC[C@H]1CCC[C@@H]1CCCCCCC(=O)O]

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein are compounds having a formula:

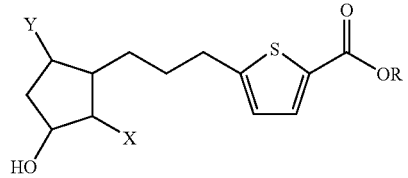

wherein R is H, or R consists of: 1) $C_{1-6}$ alkyl or phenyl, and 2) from 0 to 2 —OH moieties;
Y is —Cl, —F, —CN, or —$CF_3$; and
X consists of: 1) linear alkyl or alkenyl having from 4 to 10 carbon atoms, and 2) from 0 to 3 —OH moieties.

These compounds are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231).

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —CO$_2$(CH$_2$)$_2$OH,

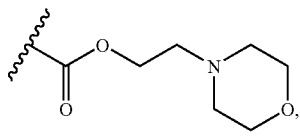

and the like.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Alkyl is a moiety consisting of carbon and hydrogen and containing no double or triple bonds.

C$_{1-6}$ alkyl is alkyl having from 1 to 6 carbon atoms.

Linear alkyl is alkyl having no branching or rings.

Alkenyl is a moiety consisting of carbon and hydrogen and containing at least one double bond, but no triple bonds.

Linear alkenyl is alkenyl having no branching or rings.

R is H, or R consists of: 1) C$_{1-6}$ alkyl or phenyl, and 2) from 0 to 2 —OH moieties.

In other words, when R is H, the compounds may have the structure below.

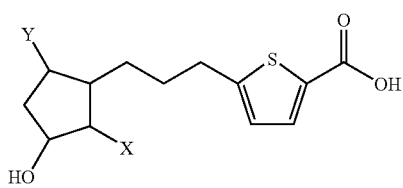

Alternatively, R consists of: 1) C$_{1-6}$ alkyl or phenyl, and 2) from 0 to 2 —OH moieties.

In other words, examples of R include:
a. —CH$_3$, —C$_2$H$_5$, —C$_3$H$_7$, —C$_4$H$_9$, —C$_5$H$_{11}$, —C$_6$H$_{13}$, cyclic —C$_3$H$_6$, cyclic —C$_4$H$_8$, cyclic —C$_5$H$_{10}$, or cyclic —C$_6$H$_{12}$, wherein "cyclic" indicates the presence of a ring;
b. —CH$_2$—OH, —C$_2$H$_4$—OH, —C$_3$H$_6$—OH, —C$_4$H$_8$—OH, —C$_5$H$_{10}$—OH, —C$_6$H$_{12}$—OH, cyclic —C$_3$H$_5$—OH, cyclic —C$_4$H$_7$—OH, cyclic —C$_5$H$_9$—OH, or cyclic —C$_6$H$_{11}$—OH, wherein the —OH may be in any position on the hydrocarbyl moiety;
c. —C$_2$H$_3$—(OH)$_2$, —C$_3$H$_5$—(OH)$_2$, —C$_4$H$_7$—(OH)$_2$, —C$_5$H$_9$—(OH)$_2$, or —C$_6$H$_{11}$—(OH)$_2$, cyclic —C$_3$H$_4$—(OH)$_2$, cyclic —C$_4$H$_6$—(OH)$_2$, cyclic —C$_5$H$_8$—(OH)$_2$, or cyclic —C$_6$H$_{10}$—(OH)$_2$, wherein —(OH)$_2$ represents 2 distinct —OH moieties, and each —OH may be in any position on the hydrocarbyl moiety; or
d.

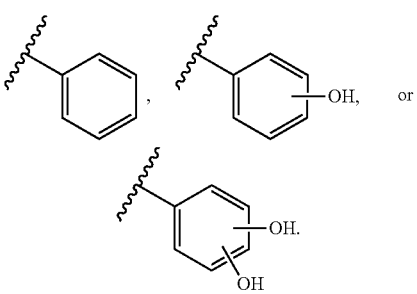

Any arrangement of carbon and hydrogen is possible provided that each carbon atom has four bonds (a double bond counts as 2 bonds for each carbon forming the bond, and a triple bond counts as 3 bonds for each carbon forming the bond), and hydrogen is always attached solely to a single carbon atom by a single bond. Each —OH attaches to a carbon atom, provided that 2 —OH moieties do not attach to the same carbon atom. Thus, many of these groups actually represent a variety of isomers. For example, each of —C$_3$H$_7$, —C$_4$H$_9$, —C$_5$H$_{11}$, and —C$_6$H$_{13}$ represent more than one isomer. Similarly for each —OH present, an additional number of isomers is introduced depending upon which carbon atom it is attached to.

Y is —Cl, —F, —CN, or —CF$_3$.

In one embodiment, Y is —Cl.

In another embodiment Y is —F.

In another embodiment Y is —CN.

In another embodiment Y is —CF$_3$.

X consists of: 1) linear alkyl or alkenyl having from 4 to 10 carbon atoms, and 2) from 0 to 3 —OH moieties.

In other words, examples of X include:
e. —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, —(CH$_2$)$_9$CH$_3$;
f. linear isomers of —C$_4$H$_8$, —C$_5$H$_{10}$, —C$_6$H$_{12}$, —C$_7$H$_{14}$, —C$_8$H$_{16}$, —C$_8$H$_{18}$, or —C$_{10}$H$_{20}$ containing a double bond;
g. a or b above containing 1 —OH attached to any carbon atom in place of a hydrogen;
h. a or b above containing 2 —OH moieties, each attached to any carbon in place of a hydrogen;
i. a or b above containing 3 —OH moieties, each attached to any carbon in place of a hydrogen;
provided that there are no more than 1 —OH on any given carbon atom, In one embodiment X is —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, or —(CH$_2$)$_9$CH$_3$.

In another embodiment X is —CH═CH(CH$_2$)$_n$—Z, wherein n is 3, 4, 5, 6, 7 or 8, and Z is —H or —OH.

In another embodiment, X is —(CH$_2$)$_p$—OH, wherein p is 4, 5, 6, 7, or 8.

In another embodiment, X is —CH$_2$)$_q$CH═CH$_2$, wherein q is 4, 5, 6, 7, or 8.

In another embodiment, X is cis —CH═CHCHOH (CH$_2$)$_r$CH$_3$, wherein r is 0, 1, 2, 3, 4, 5, or 6. 2.

In one embodiment, X consists of: 1) linear alkyl or alkenyl having from 4 to 10 carbon atoms, and 2) from 0 to 1 —OH moieties.

Another embodiment is a compound having a formula:

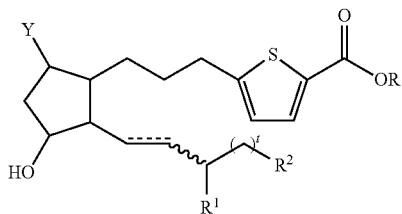

wherein a dashed line indicates the presence or absence of a bond, a wavy line indicates a cis or a trans configuration;

R$^1$ is —H, or —OH;

R$^2$ is —CH$_2$CH$_3$, —CH$_2$CH$_2$OH, or —CH═CH$_2$;

t is 0, 1, 2, 3, 4, or 5.

Another embodiment is a compound having a formula:

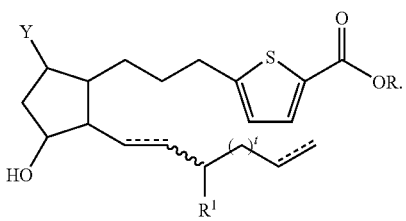

Another embodiment is a compound having a formula:

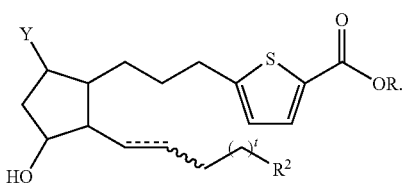

Another embodiment is a compound having a formula:

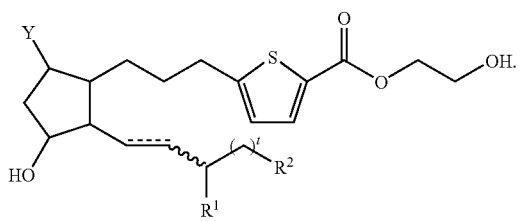

The following are examples of useful compounds.

5-[3-((1R,2R,3R,5R)-5-Chloro-3-hydroxy-2-pentyl-cyclopentyl)-propyl]-thiophene-2-carboxylic acid (entry 1, table 1)

5-[3-((1R,2R,3R,5R)-5-Chloro-2-hexyl-3-hydroxy-cyclopentyl)-propyl]-thiophene-2-carboxylic acid (entry 2, table 1)

5-[3-((1R,2R,3R,5R)-5-Chloro-2-heptyl-3-hydroxy-cyclopentyl)-propyl]-thiophene-2-carboxylic acid (entry 3, table 1)

5-[3-((1R,2R,3R,5R)-5-Chloro-3-hydroxy-2-octyl-cyclopentyl)-propyl]-thiophene-2-carboxylic acid (entry 4, table 1)

5-[3-((1R,2R,3R,5R)-5-Chloro-3-hydroxy-2-nonyl-cyclopentyl)-propyl]-thiophene-2-carboxylic acid (entry 5, table 1)

5-{3-[(1R,2R,3R,5R)-5-Chloro-3-hydroxy-2-(8-hydroxy-oct-1-enyl)-cyclopentyl]-propyl}-thiophene-2-carboxylic acid (entry 6, table 1)

5-[3-((1R,2R,3R,5R)-5-Chloro-3-hydroxy-2-pent-1-enyl-cyclopentyl)-propyl]-thiophene-2-carboxylic acid (entry 7, table 1)

5-[3-((1R,2R,3R,5R)-5-Chloro-2-hept-1-enyl-3-hydroxy-cyclopentyl)-propyl]-thiophene-2-carboxylic acid (entry 8, table 1)

5-[3-((1R,2R,3R,5R)-5-Chloro-2-dec-1-enyl-3-hydroxy-cyclopentyl)-propyl]-thiophene-2-carboxylic acid (entry 9, table 1)

5-{3-[(1R,2R,3R,5R)-5-Chloro-3-hydroxy-2-(8-hydroxy-octyl)-cyclopentyl]-propyl}-thiophene-2-carboxylic acid (entry 10, table 1)

5-{3-[(1R,2R,3R,5R)-5-Chloro-3-hydroxy-2-(7-hydroxy-heptyl)-cyclopentyl]-propyl}-thiophene-2-carboxylic acid (entry 11, table 1)

5-[3-((1R,2R,3R,5R)-5-Chloro-3-hydroxy-2-oct-7-enyl-cyclopentyl)-propyl]-thiophene-2-carboxylic acid (entry 12, table 1)

5-{3-[(1R,2R,3R,5R)-5-Chloro-3-hydroxy-2-(7-hydroxy-hept-1-enyl)-cyclopentyl]-propyl}-thiophene-2-carboxylic acid (entry 13, table 1)

5-[3-((1R,2R,3R,5R)-5-Chloro-3-hydroxy-2-non-1-enyl-cyclopentyl)-propyl]-thiophene-2-carboxylic acid (entry 14, table 1)

5-{3-[(1R,2R,3R,5R)-5-Chloro-3-hydroxy-2-((E)-(R)-3-hydroxy-oct-1-enyl)-cyclopentyl]-propyl}-thiophene-2-carboxylic acid (entry 15/16, table 1)

5-{3-[(1R,2R,3R,5R)-5-Chloro-3-hydroxy-2-((E)-(S)-3-hydroxy-oct-1-enyl)-cyclopentyl]-propyl}-thiophene-2-carboxylic acid (entry 15/16, table 1)

Ethyl 2-(2-((1R,2R,3R,5R)-5-chloro-3-hydroxy-2-octylcyclopentyl)ethylthio)thiazole-4-carboxylate (6-7, entry 17, table 1)

5-(3-((1R,2R,3R,5R)-5-chloro-3-hydroxy-2-((E)-oct-3-enyl)cyclopentyl)propyl)thiophene-2-carboxylic acid (7-4, entry 18, table 1)

5-(3-((1R,2R,3R,5R)-5-chloro-2-decyl-3-hydroxycyclopentyl)propyl)thiophene-2-carboxylic acid (entry 19, table 1)

The following examples are intended only to illustrate the invention and should in no way be construed as limiting the invention.

EXAMPLES

Synthetic Methods

While there are many ways to prepare the compounds disclosed herein, useful compounds may be obtained by using or adapting the following exemplary procedures.

Scheme 1

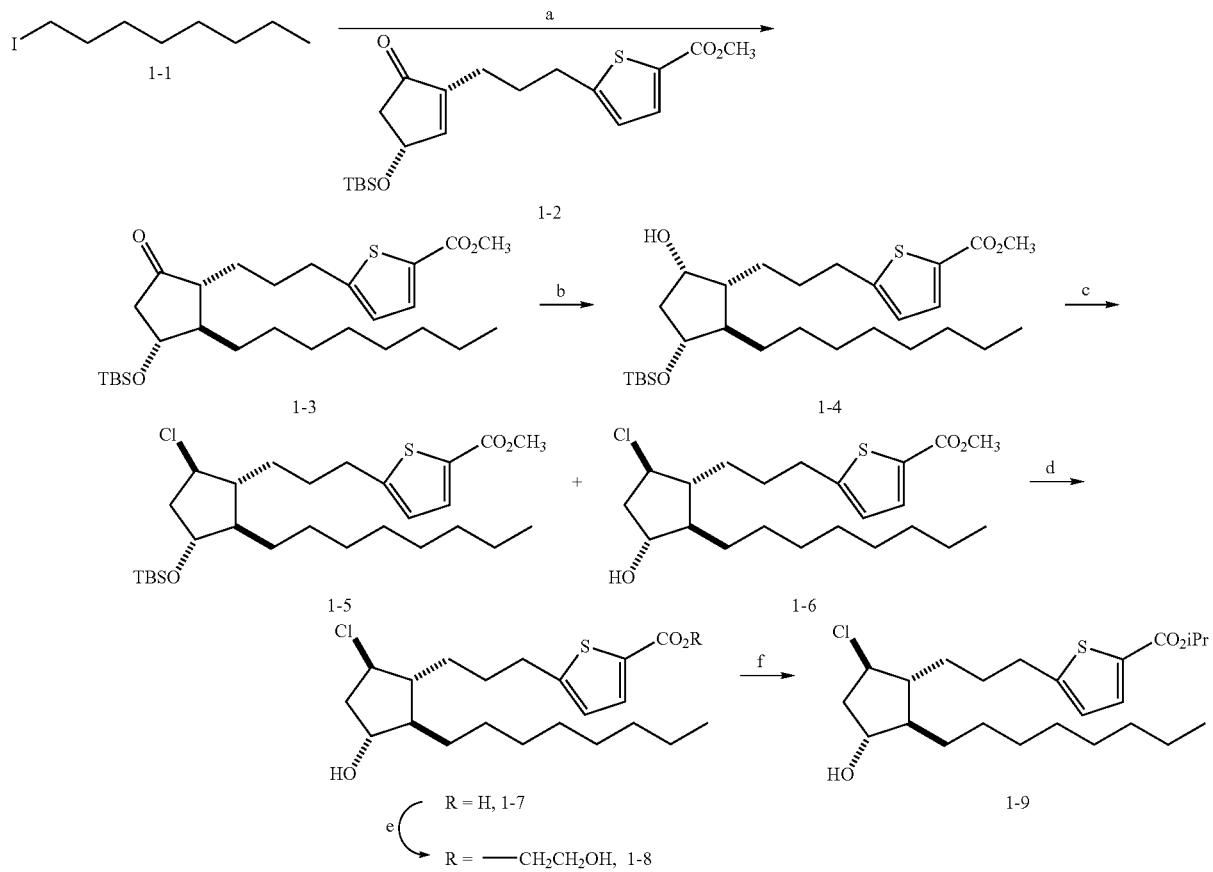

(a) t-BuLi; 2-ThienylCuCNLi; (b) L-selectride; (c) MsCl, TEA; TBAC 55° C.; (d) 1 M LiOH, THF 60° C; (e) ClCO₂Et, Et₃N; ethylene glycol; (f) DBU, 2-iodopropane, acetone.

Scheme 1: 1,4-addition method (used to prepare entries 2, 4 and 12 from table 1).

5-{3-[(1R,2R,3R)-3-(tert-Butyl-dimethyl-silanyloxy)-2-octyl-5-oxo-cyclopentyl]-propyl}-thiophene-2-carboxylic acid methyl ester (1-3). tert-Butyllithium (2 mL, 3.4 mmol, 1.7 M/pentane) was added to a −78° C. solution of 1-iodooctane (310 mL, 1.7 mmol) in ether (3.4 mL). The reaction was stirred for 30 min. and then a solution of 2-thienylCuCNLi (6 mL, 1.92 mmol, 0.32 M/THF, prepared as previously described in U.S. Pat. No. 7,091,231) was added. The reaction was stirred for 10 min. at 0° C. and was then recooled to −78° C. At this time, a solution of enone 2 (510 mg, 1.29 mmol, prepared as previously described in US 20060205800) in ether (1.4 mL) was added drop wise by cannula, rinsing with 0.6 mL ether. The resulting mixture was stirred at −78° C. for 30 min., at 0° C. for 40 min., and at room temperature for 30 min. The reaction was quenched by addition of saturated NH₄Cl solution (15 mL) and the resulting mixture was extracted with ethyl acetate (3×30 mL). The combined ethyl acetate solution was dried (Na₂SO₄), filtered and evaporated. Purification by flash chromatography on silica gel (0%→40% ethyl acetate/hexanes) gave the title compound (558 mg, 85%).

The remainder of the compounds in scheme 1, with the exception of 1-8 (procedure described below), were prepared as described previously (U.S. Pat. No. 7,091,231 and US 20060205800, the entire contents of which are incorporated herein by reference).

5-[3-((1R,2R,3R,5R)-5-Chloro-3-hydroxy-2-octyl-cyclopentyl)-propyl]-thiophene-2-carboxylic acid 2-hydroxy-ethyl ester (1-8). A solution of ethyl chloroformate in CH₂Cl₂ (0.5 mL of a 8 μL/mL solution, 0.042 mmol) was added to 1-7 (14 mg, 0.035 mmol). Triethylamine (40 μL, 0.29 mmol) was added and after 1 h, ethylene glycol (100 μL, 1.79 mmol) was added. The reaction was allowed to stir for 3 days and then 1 M HCl (4 mL) was added. The resulting mixture was extracted with CH₂Cl₂ (3×20 mL) and the combined CH₂Cl₂ solution was washed with brine (20 mL), dried (Na₂SO₄), filtered and evaporated. Purification of the residue by flash chromatography on silica gel (0%→15% methanol/CH₂Cl₂) gave the title compound (5 mg, 32%) along with 1-7 (8 mg, 57%).

Scheme 2

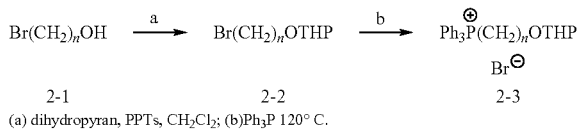

(a) dihydropyran, PPTs, CH₂Cl₂; (b)Ph₃P 120° C.

Scheme 2: (Phosphonium salts used in the Wittig synthesis of entries 6,10,11,13).

2-(7-Bromo-heptyloxy)-tetrahydro-pyran (2-2, n=7). Dihydropyran (1 mL, 11.0 mmol) and pyridinium p-toluenesulfonate (148 mg, 0.59 mmol) were added to a solution of 7-Bromo-1-heptanol (1.1 g, 5.64 mmol) in CH$_2$Cl$_2$ (22 mL). After stirring overnight, the solution was washed with 1 M HCl (20 mL), saturated NaHCO$_3$ solution (20 mL) and brine (20 mL). The solution was dried (Na$_2$SO$_4$), filtered and evaporated. The residue was purified by flash chromatography on silica gel (0%→50% ethyl acetate/hexanes) to give the title compound (1.8 g, >100%).

Triphenyl(7-(tetrahydro-2H-pyran-2-yloxy)heptyl)phosphonium Bromide (2-3, n=7). A mixture of 2-2 (1.8 g, <5.64 mmol) and Ph$_3$P (1.715 g, 6.54 mmol) was heated at 120° C. overnight. The mixture was allowed to cool to room temperature and was purified by flash chromatography on silica gel (0%→30% methanol/CH$_2$Cl$_2$) to give the title compound (1.174 g, 2.17 mmol, 38% from 7-Bromo-1-heptanol).

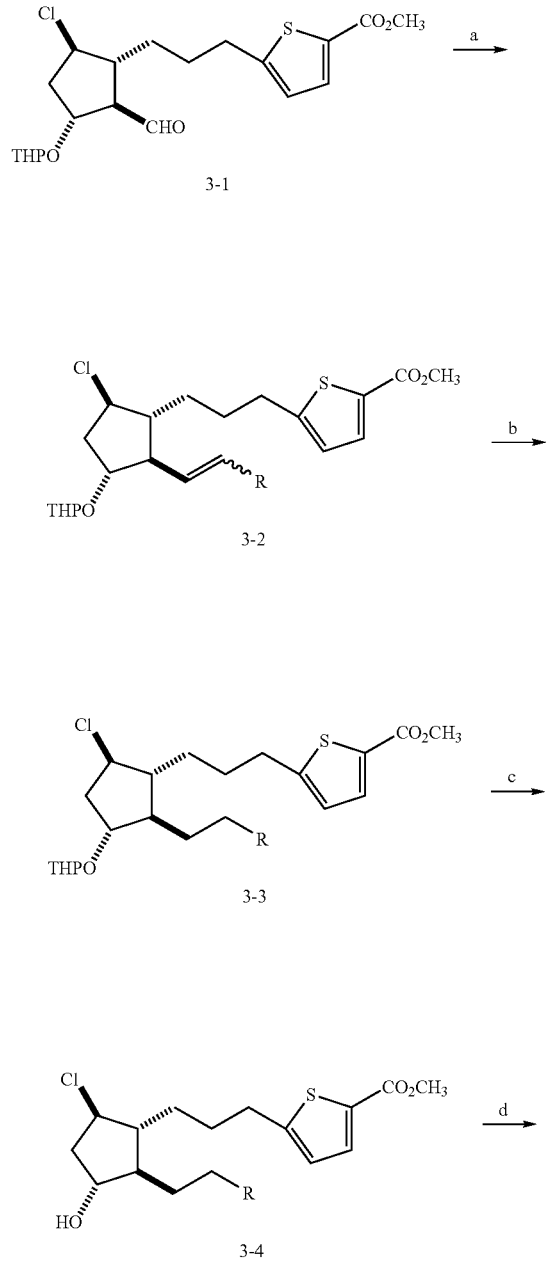

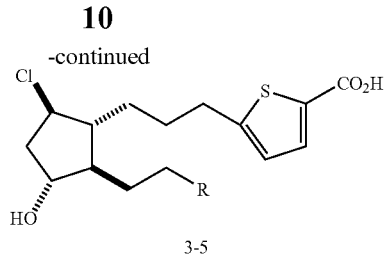

(a) RCH$_2$PPh$_3$$^+$X$^-$, KOtBu, THF; (b) H$_2$, Pd/C; (c) PPTs, MeOH; (d) 1 M LiOH, THF 60° C.

Scheme 3: Wittig synthesis (used to prepare entries 1, 3, 5, 6, 7, 8, 9, 10, 11, 13, 14, 19 [table 1]).

5-{3-[(1R,2R,3R,5R)-5-Chloro-2-non-1-enyl-3-(tetrahydro-pyran-2-yloxy)-cyclopentyl]-propyl}-thiophene-2-carboxylic acid methyl ester (3-2, R═(CH$_2$)$_6$CH$_3$). Octyltriphenylphosphonium bromide (454 mg, 1.0 mmol, Alfa Aesar) was dried under vacuum (0.4 mbar) for 3 days. The dried salt was taken into 3 mL THF and a solution of tert-BuOK (900 μL, 0.9 mmol, 1 M/THF) was added. The resulting red-orange solution was stirred for 45 min. and then a solution of aldehyde 3-1 (111 mg, 0.27 mmol, U.S. Provisional Patent Application No. 60/947,904, filed Jul. 3, 2007) in 1 mL THF was added by cannula, rinsing with 1 mL THF. The reaction was allowed to stir for 1.5 h and was then quenched by addition of 5 mL saturated NH$_4$Cl solution. The mixture was extracted with ethyl acetate (3×20 mL) and the combined organic solution was dried (Na$_2$SO$_4$), filtered and evaporated. Purification by flash chromatography on silica gel (0%→50% ethyl acetate/hexanes) gave 101 mg (74%) of the title compound.

5-{3-[(1R,2R,3R,5R)-5-Chloro-2-heptyl-3-(tetrahydropyran-2-yloxy)-cyclopentyl]-propyl}-thiophene-2-carboxylic acid methyl ester (3-3, R═—(CH$_2$)$_4$CH$_3$). Pd/C (17 mg, 10%) was added to a solution of 3-2 (R═(CH$_2$)$_4$CH$_3$, 20 mg, 0.04 mmol) in methanol (2 mL). The reaction was placed under 1 atm H$_2$ (balloon) and after 5 h, was filtered through Celite and evaporated. The reaction was incomplete and so was resubmitted to the reaction conditions (17 mg Pd/C and 2 mL methanol). After overnight stirring, the mixture was filtered through Celite and evaporated. The residue was purified by flash chromatography on silica gel (0%→50% ethyl acetate/hexanes) to give the title compound (25 mg, >100%).

5-[3-((1R,2R,3R,5R)-5-Chloro-2-heptyl-3-hydroxy-cyclopentyl)-propyl]-thiophene-2-carboxylic acid methyl ester (3-4, R═—(CH$_2$)$_4$CH$_3$). PPTs (8 mg, 0.032 mmol) was added to a methanol (1 mL) solution of 3-3 (R═—(CH$_2$)$_4$CH$_3$, 25 mg, 0.051 mmol). The solution was stirred at 40° C. overnight and then was evaporated. Purification of the residue by flash chromatography on silica gel (0%→50% ethyl acetate/hexanes) gave the title compound (18 mg, 87%).

5-[3-((1R,2R,3R,5R)-5-Chloro-2-heptyl-3-hydroxy-cyclopentyl)-propyl]-thiophene-2-carboxylic acid (3-5, R═—(CH$_2$)$_4$CH$_3$). The previously described LiOH procedure was used (US 20060205800).

Scheme 4

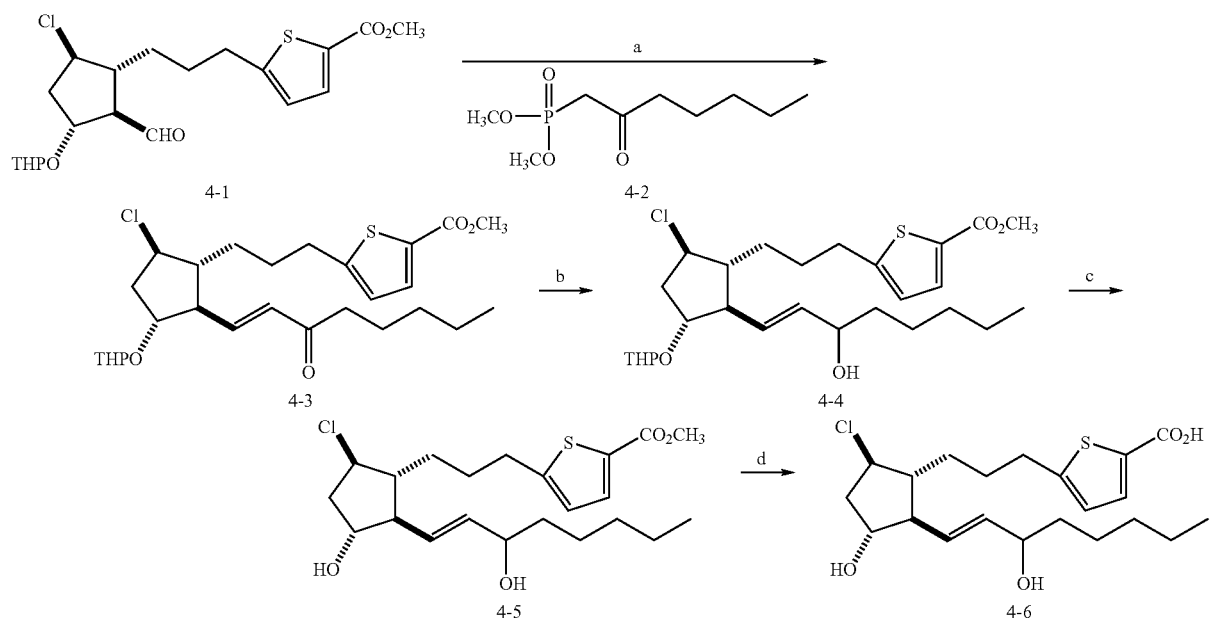

(a) 4-2, NaH, THF; (b) NaBH₄, MeOH; (c) PPTs, MeOH; separate diastereomers; (d) 1 M LiOH, THF 60° C.

5-{3-[(1R,2R,3R,5R)-5-Chloro-2-((E)-3-oxo-oct-1-enyl)-3-(tetrahydro-pyran-2-yloxy)-cyclopentyl]-propyl}-thiophene-2-carboxylic acid methyl ester (4-3). A solution of phosphonate 4-2 (40 µL, 0.19 mmol) in 2.2 mL THF was added to an ice cold mixture of NaH (9 mg, 0.23 mmol, 60%/oil) in 1.6 mL THF by cannula. The mixture was allowed to warm to room temperature and after 1 h, was recooled to 0° C. At this time, a solution of aldehyde 3-1 (80 mg, 0.19 mmol) in 0.6 mL THF was added by cannula, rinsing with 0.6 mL THF. The reaction was allowed to warm to room temperature and after stirring overnight, was quenched by addition of 10 mL saturated NH₄Cl solution. The resulting mixture was extracted with ethyl acetate (3×25 mL) and the combined ethyl acetate solution was dried (Na₂SO₄), filtered and evaporated. Purification by flash chromatography on silica gel (0%→100% ethyl acetate/hexanes) gave the title compound (59 mg, 60%).

5-{3-[(1R,2R,3R,5R)-5-Chloro-2-((E)-3-hydroxy-oct-1-enyl)-3-(tetrahydro-pyran-2-yloxy)-cyclopentyl]-propyl}-thiophene-2-carboxylic acid methyl ester (4-4). NaBH₄ (9.2 mg, 0.24 mmol) was added to a solution of ketone 4-3 (59 mg, 0.12 mmol) in methanol (1 mL). The reaction was stirred at room temperature for 2 h and then was quenched by addition of 5 mL 1 M HCl. The resulting mixture was extracted with CH₂Cl₂ and the combined CH₂Cl₂ solution was dried (Na₂SO₄), filtered and evaporated. Purification by flash chromatography on silica gel (ethyl acetate/hexanes) gave the title compound (48 mg, 80%).

5-{3-[(1R,2R,3R,5R)-5-Chloro-3-hydroxy-2-((E)-(S)-3-hydroxy-oct-1-enyl)-cyclopentyl]-propyl}-thiophene-2-carboxylic acid methyl ester and 5-{3-[(1R,2R,3R,5R)-5-Chloro-3-hydroxy-2-((E)-(R)-3-hydroxy-oct-1-enyl)-cyclopentyl]-propyl}-thiophene-2-carboxylic acid methyl ester (4-5). The PPTs/methanol procedure described for scheme 3 was used. Purification of the crude product by flash chromatography on silica gel (0%→100% ethyl acetate/hexanes) gave the individual diastereomers: (higher Rf, 17 mg, 41%) and (lower Rf, 17 mg, 41%).

5-{3-[(1R,2R,3R,5R)-5-Chloro-3-hydroxy-2-((E)-(S)-3-hydroxy-oct-1-enyl)-cyclopentyl]-propyl}-thiophene-2-carboxylic acid and 5-{3-[(1R,2R,3R,5R)-5-Chloro-3-hydroxy-2-((E)-(R)-3-hydroxy-oct-1-enyl)-cyclopentyl]-propyl}-thiophene-2-carboxylic acid (4-6). The individual diastereomers were hydrolyzed to the corresponding acids (61% for the higher Rf diastereomer and 81% for the lower Rf diastereomer) using the previously described LiOH procedure (US 20060205800).

Scheme 5

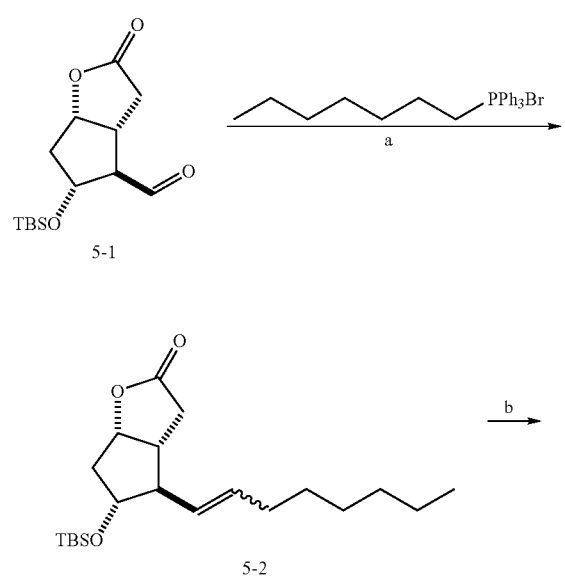

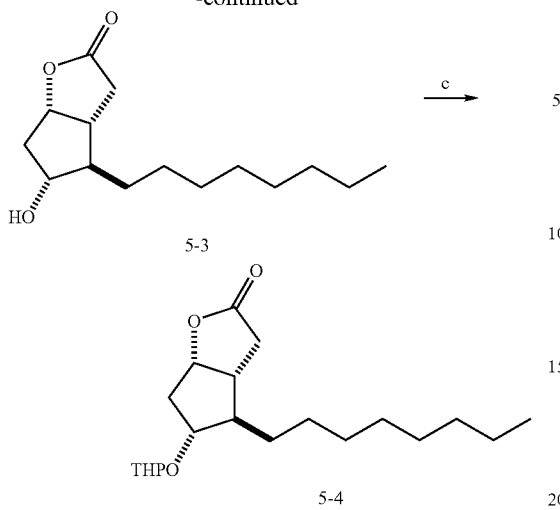

5-3

(a) tert-BuOK, THF; (b) H₂, Pd/C, MeOH; (c) dihyropyran, PPTs, CH₂Cl₂.

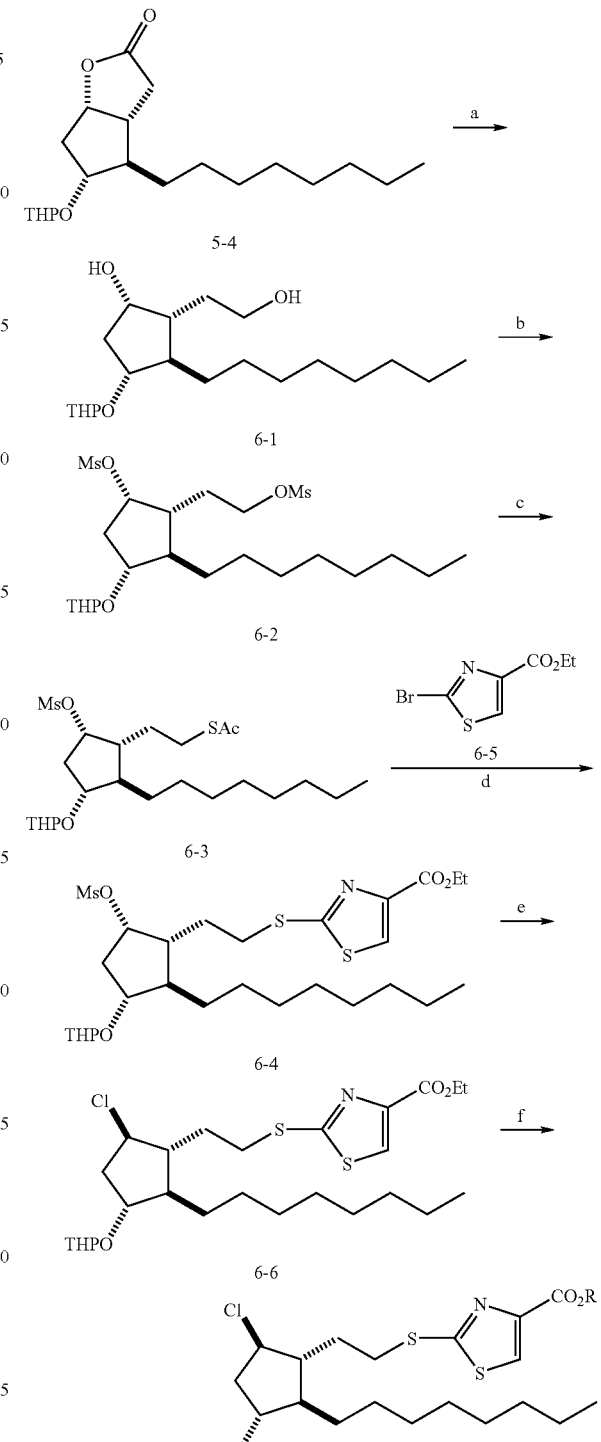

Scheme 6

(a) LiAlH₄, THF 0° C.; (b) MsCl, Et₃N, CH₂Cl₂; (c) KSAc, DMF; (d) PBu₃, K₂CO₃, EtOH 40° C.; (e) Bu₄NCl, toluene 55° C.; (f) PPTs, MeOH 40° C.; (g) 1 M LiOH, THF.

(3aR,4R,5R,6aS)-5-(tert-butyldimethylsilyloxy)-4-(oct-1-enyl)hexahydro-2H-cyclopenta[b]furan-2-one (5-2). n-heptylphosphonium bromide (3.185 g, 7.22 mmol) was dried under vacuum for 3 days and was then taken into dry THF (22 mL). Potassium tert-butoxide (7.2 mL, 7.2 mmol, 1 M/THF) was added and the resulting red-orange solution was stirred for 45 min. at room temperature. A solution of (3aR,4R,5R,6aS)-5-(tert-butyldimethylsilyloxy)-2-oxohexahydro-2H-cyclopenta[b]furan-4-carbaldehyde (5-1, 502 mg, 1.78 mmol, Cayman) in 7 mL THF was added by cannula, rinsing with 3 mL THF. After 1.5 h, the reaction was quenched by addition of saturated NH₄Cl solution. The resulting mixture was extracted with ethyl acetate (3×) and the combined ethyl acetate solution was dried (Na₂SO₄), filtered and evaporated. Purification of the residue by flash chromatography on silica gel (Isco Combiflash unit) gave the title compound (595 mg, 91%).

(3aR,4R,5R,6aS)-5-hydroxy-4-octylhexahydro-2H-cyclopenta[b]furan-2-one (5-3). A mixture of 5-2 (595 mg, 1.62 mmol) and 5% Pd/C (556 mg, 0.17 mmol) in methanol (80 mL) was stirred under 1 atm H₂ pressure (balloon) overnight. The mixture was then filtered through Celite and the filtrate evaporated. Purification of the residue by flash chromatography on silica gel (Isco Combiflash unit) gave the title compound (396 mg, 96%).

(3aR,4R,5R,6aS)-4-octyl-5-(tetrahydro-2H-pyran-2-yloxy)hexahydro-2H-cyclopenta[b]furan-2-one (5-4). Dihydropyran (60 μL, 0.66 mmol) and PPTs (11 mg, 0.045 mmol) were added to a solution of 5-3 (81 mg, 0.32 mmol) in dichloromethane (1.2 mL). After overnight stirring, the reaction was washed with 1 M HCl, saturated NaHCO₃ solution and brine. The organic layer was dried (Na₂SO₄), filtered and evaporated. Purification of the residue by flash chromatography on silica gel (Isco Combiflash unit) gave the title compound (100 mg, 93%).

(1S,2R,3R,4R)-2-(2-hydroxyethyl)-3-octyl-4-(tetrahydro-2H-pyran-2-yloxy)cyclopentanol (6-1). A solution of LiAlH₄ (1.5 mL, 1.5 mmol, 1 M/THF) was added to a 0° C.

solution of 5-4 (453 mg, 1.34 mmol) in THF (5 mL). After 3 h, H₂O (5 mL) was added dropwise followed by dichloromethane and 15% NaOH (10 mL). The reaction was allowed to warm to room temperature and was stirred further for 30 min. The resulting mixture was extracted with dichloromethane (3×) and the combined dichloromethane solution was dried (Na$_2$SO$_4$), filtered and evaporated. Purification of the residue by flash chromatography on silica gel (Isco Combiflash unit) gave the title compound (447 mg, 97%).

2-((1R,2R,3R,5S)-5-(methylsulfonyloxy)-2-octyl-3-(tetrahydro-2H-pyran-2-yloxy)cyclopentyl)ethyl methanesulfonate (6-2). MsCl (0.60 mL, 7.72 mmol) was added to an ice cold solution of 6-1 (447 mg, 1.31 mmol) and Et$_3$N (1.3 mL, 9.33 mmol) in dichloromethane (5 mL). The reaction was allowed to warm to room temperature and after 3 h, saturated NaHCO$_3$ solution was added. The resulting mixture was extracted with dichloromethane (3×) and the combined dichloromethane solution was dried (Na$_2$SO$_4$), filtered and evaporated. Purification of the residue by flash chromatography on silica gel (Combiflash unit by Isco) gave the title compound (326 mg, 50%).

S-2-((1R,2R,3R,5S)-5-(methylsulfonyloxy)-2-octyl-3-(tetrahydro-2H-pyran-2-yloxy)cyclopentyl)ethyl ethanethioate (6-3). KSAc (115 mg, 1.01 mmol) was added to a solution of 6-2 (326 mg, 0.65 mmol) in 8 mL DMF. The reaction was allowed to stir overnight and then 20 mL H$_2$O was added. The resulting mixture was extracted with ethyl acetate (3×20 mL) and the combined ethyl acetate solution was washed with H$_2$O (3×60 mL) and brine (50 mL). The solution was then dried (Na$_2$SO$_4$), filtered and evaporated. Purification by flash chromatography on silica gel (Combiflash unit by Isco) gave the title compound (183 mg, 58%).

Ethyl 2-(2-((1R,2R,3R,5S)-5-(methylsulfonyloxy)-2-octyl-3-(tetrahydro-2H-pyran-2-yloxy)cyclopentyl)ethylthio)thiazole-4-carboxylate (6-4). PBu$_3$ (20 µL, 0.08 mmol), ethyl 2-bromothiazole-4-carboxylate (6-5, 119 mg, 0.50 mmol) and K$_2$CO$_3$ (107 mg, 0.77 mmol) were added to a solution of 6-3 (183 mg, 0.38 mmol) in 1.6 mL ethanol. The mixture was stirred at 40° C. overnight and then 20 mL H$_2$O was added. The resulting mixture was extracted with ethyl acetate (30 mL) and the ethyl acetate solution was washed with brine (20 mL). The solution was then dried (Na$_2$SO$_4$), filtered, and evaporated. Purification of the residue by flash chromatography on silica gel (Combiflash unit by Isco) gave the title compound (41 mg, 18%).

Ethyl 2-(2-((1R,2R,3R,5R)-5-chloro-2-octyl-3-(tetrahydro-2H-pyran-2-yloxy)cyclopentyl)ethylthio)thiazole-4-carboxylate (6-6). A mixture of 6-4 (41 mg, 0.069 mmol) and tetra-n-butylammonium chloride (200 mg, 0.72 mmol) in 1 mL toluene was stirred at 55° C. overnight. The mixture was allowed to cool to room temperature and was filtered through Celite, washing with ethyl acetate. The filtrate was evaporated and the residue was purified by flash chromatography on silica gel (Isco Combiflash unit) to give the title compound (24 mg, 65%).

Ethyl 2-(2-((1R,2R,3R,5R)-5-chloro-3-hydroxy-2-octylcyclopentyl)ethylthio)thiazole-4-carboxylate (6-7). A similar procedure as that described for compound 3-4 was used, starting with 24 mg 6-6 and providing (13 mg, 67%) of 6-7.

2-(2-((1R,2R,3R,5R)-5-chloro-3-hydroxy-2-octylcyclopentyl)ethylthio)thiazole-4-carboxylic acid (6-8). The previously described LiOH procedure (U.S. Pat. No. 7,091,231) was used, starting with 13 mg 6-7 and providing 6-8 (13 mg, 100%).

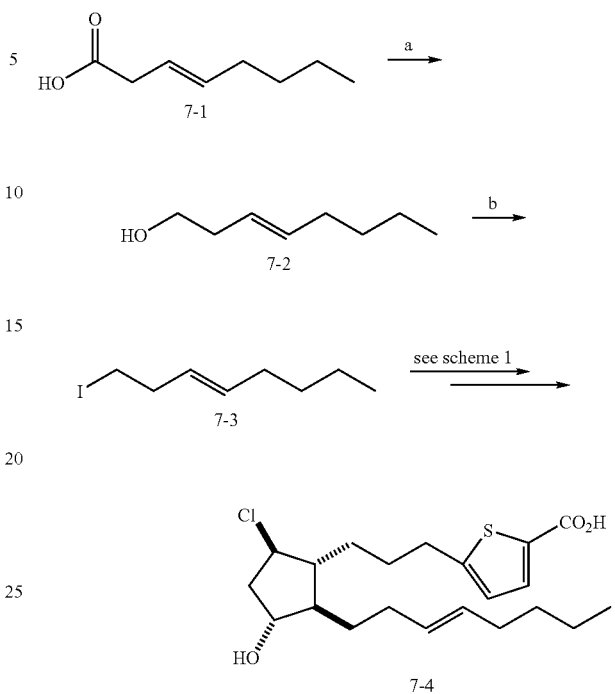

Scheme 7

(a) LiAlH$_4$, THF; (b) Ph$_3$P, I$_2$, imidazole, CH$_2$Cl$_2$.

(E)-oct-3-en-1-ol (7-2). LiAlH$_4$ (13.5 mL, 13.5 mmol, 1 M/THF) was added to an ice cold solution of (E)-oct-3-enoic acid (7-1, 1.86 g, 13.1 mmol) in THF (48 mL). The reaction was allowed to warm to room temperature and after 2 h, was cooled in an ice bath and 50 mL H$_2$O was added slowly. NaOH (3 M, 50 mL) and H$_2$O (50 mL) were added and the resulting mixture was extracted with dichloromethane (3×100 mL). The combined organic layer was washed with brine (100 mL) and was then dried (Na$_2$SO$_4$), filtered and evaporated. Purification of the residue by flash chromatography on silica gel (Isco Combiflash unit) gave the title compound (1.283 g, 76%).

(E)-1-iodooct-3-ene (7-3). A mixture of Ph$_3$P (3.205 g, 12.2 mmol), imidazole (1.221 g, 17.9 mmol), and I$_2$ (3.024 g, 11.9 mmol) in CH$_2$Cl$_2$ (38 mL) was stirred at room temperature. After 15 min., a solution of 7-2 (1.283 g, 10.0 mmol) in CH$_2$Cl$_2$ (4.8 mL) was added by cannula, rinsing with 4 mL CH$_2$Cl$_2$. After 3 h, the mixture was filtered through basic alumina, washing with 10% ethyl acetate/hexanes. The filtrate was evaporated and the residue was purified by flash chromatography on silica gel (Isco Combiflash unit) to provide the title compound (2.323 g, 98%).

5-(3-((1R,2R,3R,5R)-5-chloro-3-hydroxy-2-((E)-oct-3-enyl)cyclopentyl)propyl)thiophene-2-carboxylic acid (7-4). The title compound was prepared as described for 1-7 in scheme 1.

In Vitro Examples

U.S. patent application Ser. No. 11/553,143, filed on Oct. 26, 2006, incorporated by reference herein, describes the methods used to obtain the in vitro data in Table 1 below.

TABLE 1

| Entry | STRUCTURE | EP2 cAMP EC50 (nM) | EP2 Ki (nM) | EP2 Ca2+ EC50 (nM) | EP4 Ca2+ EC50 (nM) | EP4 Ki (nM) | OTHER RECEPTORS Ca2+ EC50 (nM) |
|---|---|---|---|---|---|---|---|
| 1 | 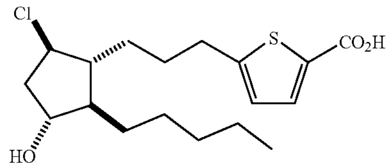 [SMILES: CCCCC[C@@H]1[C@@H](CCCc2ccc(C(=O)O)s2)[C@H](Cl)C[C@H]1O] | 1 | 6 | 74 | 9099 | NA | DP(2084), EP3(1742), TP(187) NA: EP1, FP, IP |
| 2 | 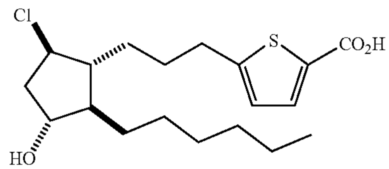 [SMILES: CCCCCC[C@@H]1[C@@H](CCCc2ccc(C(=O)O)s2)[C@H](Cl)C[C@H]1O] | 0.7 | 4 | 405 | 9380 | 754 | EP3(5994), DP(1781), TP(2986) NA: EP1, FP, IP |
| 3 | 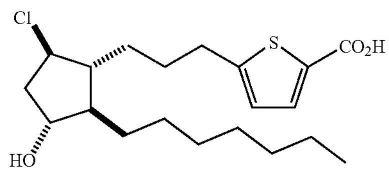 [SMILES: CCCCCCC[C@@H]1[C@@H](CCCc2ccc(C(=O)O)s2)[C@H](Cl)C[C@H]1O] | 2 | 3 | 67 | 7508 | 330 | DP(2246), EP1(3391), EP3(6658), FP(10K), IP(>10K)TP(10K) |
| 4 | 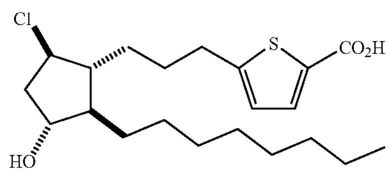 [SMILES: CCCCCCCC[C@@H]1[C@@H](CCCc2ccc(C(=O)O)s2)[C@H](Cl)C[C@H]1O] | 0.4 | 0.5 | 11 | 11,437 | 395 | EP1(18,214), EP3(9526), DP(6768) NA: FP, IP, TP |
| 5 | 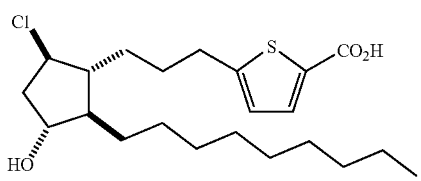 | 3 | 1.5 | 21 | >10K | 1225 | EP3(6661) NA: EP1, DP, FP, IP, TP |
| 6 | 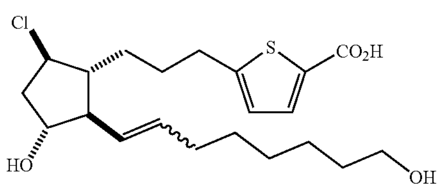 [SMILES: O=C(O)c1ccc(CCC[C@@H]2[C@@H](C=CCCCCCCO)[C@H](O)C[C@H]2Cl)s1] | 14 | 37 | 531 | | NA | EP1(>10K), DP (1003) NA: EP3, FP, IP, TP |
| 7 | 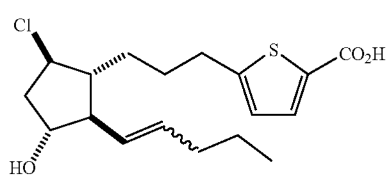 [SMILES: CCCC=C[C@@H]1[C@@H](CCCc2ccc(C(=O)O)s2)[C@H](Cl)C[C@H]1O] | 55 | 60 | 303 | 14,784 | NA | DP(573), EP3(1158), TP(249) NA: EP1, FP, IP |
| 8 | 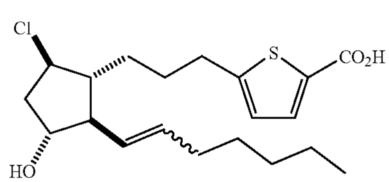 [SMILES: CCCCCC=C[C@@H]1[C@@H](CCCc2ccc(C(=O)O)s2)[C@H](Cl)C[C@H]1O] | 8 | 14 | 112 | 9,100 | 186 | EP3(544), DP(337), TP(230), NA: EP1, FP, IP |

TABLE 1-continued

| Entry | STRUCTURE | EP2 cAMP EC50 (nM) | EP2 Ki (nM) | EP2 Ca2+ EC50 (nM) | EP4 Ca2+ EC50 (nM) | EP4 Ki (nM) | OTHER RECEPTORS Ca2+ EC50 (nM) |
|---|---|---|---|---|---|---|---|
| 9 | 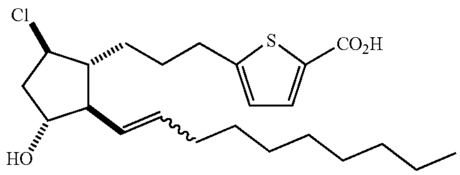 [SMILES: CCCCCCCCC=C[C@@H]1[C@@H](CCCc2ccc(C(=O)O)s2)[C@H](Cl)C[C@H]1O] | 15 | 18 | 512 | 34,171 | 695 | DP(10,544) NA: EP1, EP3, FP, IP, TP |
| 10 | 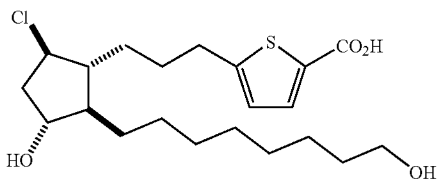 [SMILES: O=C(O)c1ccc(CCC[C@@H]2[C@@H](CCCCCCCCO)[C@H](O)C[C@H]2Cl)s1] | <1 | 5 | 69 | <10K | | DP(6133) NA: EP1, EP3, FP, IP, TP |
| 11 | 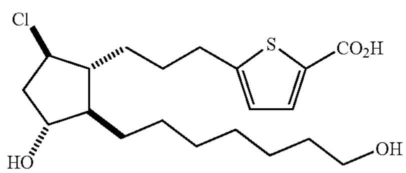 [SMILES: O=C(O)c1ccc(CCC[C@@H]2[C@@H](CCCCCCCO)[C@H](O)C[C@H]2Cl)s1] | 0.3 | 9 | 10 | 23,665 | 1518 | DP(1946) NA: EP1, EP3, FP, IP, TP |
| 12 | 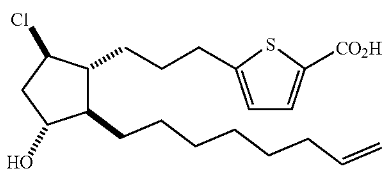 [SMILES: C=CCCCCCC[C@@H]1[C@@H](CCCc2ccc(C(=O)O)s2)[C@H](Cl)C[C@H]1O] | 0.2 | 3 | 7 | 6466 | 351 | DP(3208), EP1(883), EP3(4990), FP(7570), TP(10,297) NA: IP |
| 13 | 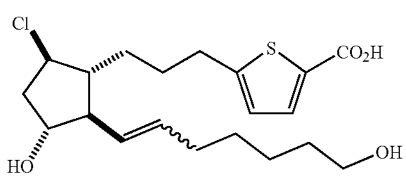 [SMILES: O=C(O)c1ccc(CCC[C@@H]2[C@@H](C=CCCCCCO)[C@H](O)C[C@H]2Cl)s1] | 3.6 | 60 | 46 | 31,351 | 2389 | DP(253), EP3(11,335) NA: EP1, EP3, FP, IP, TP |
| 14 | 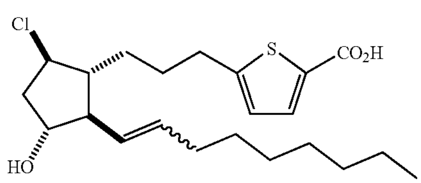 [SMILES: CCCCCCCC=C[C@@H]1[C@@H](CCCc2ccc(C(=O)O)s2)[C@H](Cl)C[C@H]1O] | 4 | 6 | 15 | >10K | 1112 | DP(11,738), EP3(2996) NA: EP1, FP, IP, TP |
| 15 | 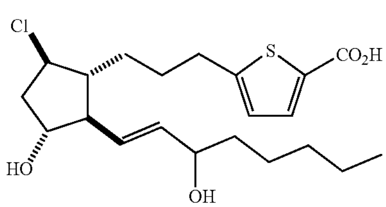 [SMILES: CCCCCC(O)/C=C/[C@@H]1[C@@H](CCCc2ccc(C(=O)O)s2)[C@H](Cl)C[C@H]1O] | 0.4 | 7 | 0.8 | 0.2 | 4 | DP(10), EP1(1.3), EP3(6), TP(178) NA: FP, IP |
| 16 | 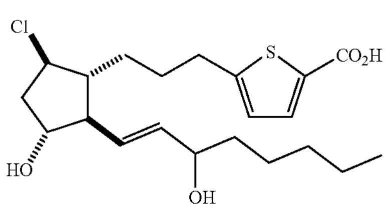 [SMILES: CCCCCC(O)/C=C/[C@@H]1[C@@H](CCCc2ccc(C(=O)O)s2)[C@H](Cl)C[C@H]1O] | 5 | 202 | 26 | 42 | 577 | DP(7732), EP1(86), EP3(421) NA: FP, IP, TP |

TABLE 1-continued

| Entry | STRUCTURE | EP2 cAMP EC50 (nM) | EP2 Ki (nM) | EP2 Ca2+ EC50 (nM) | EP4 Ca2+ EC50 (nM) | EP4 Ki (nM) | OTHER RECEPTORS Ca2+ EC50 (nM) |
|---|---|---|---|---|---|---|---|
| 17 | (structure 6-7) | 0.09 | 0.2 | 34 | 641 | 1421 | DP(842), EP1(456), EP3(329), IP(9655), TP(1067) |
| 18 | (structure 7-4) | 2 | 18 | 51 | 713 | <10K | DP(2800), EP1(4934), EP3(593) NA: FP, IP, TP |
| 19 | (structure) | 2 | 6 | 1158 | >>10K | 7103 | NA: EP1, EP3, DP, FP, IP, TP |

In Vivo Examples

U.S. Pat. No. 7,091,231, incorporated by reference herein, describes the methods used to obtain the in vivo test results presented in Table 2.

TABLE 2

| ENTRY | STRUCTURE | Conc. (g/100 mL) | DOG Max. ΔIOP (%) | DOG Max. hyperemia | MONKEY Max. ΔIOP (%) |
|---|---|---|---|---|---|
| 1 | (structure 1-7) | 0.01% | 40 | 1.3 | 31 |
| 2 | (structure 1-8) | 0.01% | 35 | 2.0 | 53 |

TABLE 2-continued

| ENTRY | STRUCTURE | Conc. (g/100 mL) | DOG Max. ΔIOP (%) | DOG Max. hyperemia | MONKEY Max. ΔIOP (%) |
|---|---|---|---|---|---|
| 3 | 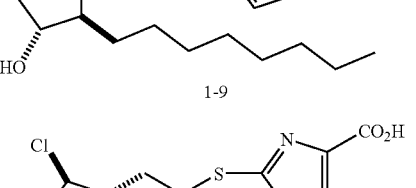 1-9 | 0.01 | 22 | 0.9 | |
| 4 | 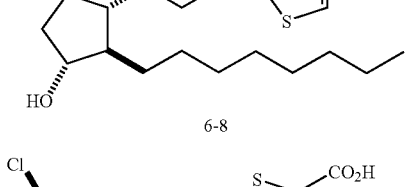 6-8 | .005% | 44 | 2.4 | 56 |
| 5 | 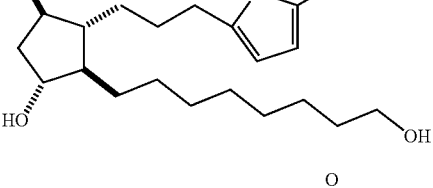 | 0.01 | 22 | 1.3 | 22 |
| 6 | 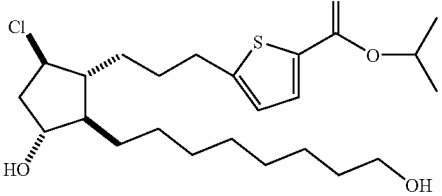 | 0.01 | 21 | 0.9 | 21 |
| 7 | 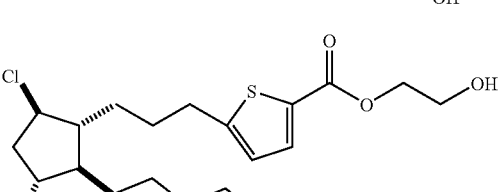 | 0.01 | 33 | 1.8 | 22 |

While this invention has been described with respect to these specific examples, it is understood that other modifications and variations are possible without departing from the spirit of the invention.

What is claimed is:

1. A compound having the formula:

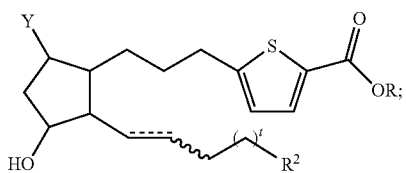

wherein:
Y is —Cl, —F, —CN, or —CF$_3$;
R is H, or R consists of: 1) C$_{1-6}$ alkyl or phenyl, and 2) from 0 to 2 —OH moieties;
the dashed line indicates the presence or absence of a bond;
the wavy line indicates a cis or a trans configuration;
R$^2$ is —CH$_2$CH$_3$, —CH$_2$CH$_2$OH, or —CH=CH$_2$; and
t is 0, 1, 2, 3, 4, or 5.

2. The compound of claim 1 selected from:
5-[3-((1R,2R,3R,5R)-5-Chloro-3-hydroxy-2-pentyl-cyclopentyl)-propyl]-thiophene-2-carboxylic acid;
5-[3-((1R,2R,3R,5R)-5-Chloro-2-hexyl-3-hydroxy-cyclopentyl)-propyl]-thiophene-2-carboxylic acid;
5-[3-((1R,2R,3R,5R)-5-Chloro-2-heptyl-3-hydroxy-cyclopentyl)-propyl]-thiophene-2-carboxylic acid;
5-[3-((1R,2R,3R,5R)-5-Chloro-3-hydroxy-2-octyl-cyclopentyl)-propyl]-thiophene-2-carboxylic acid;

5-[3-((1R,2R,3R,5R)-5-Chloro-3-hydroxy-2-nonyl-cyclopentyl)-propyl]-thiophene-2-carboxylic acid;

5-{3-[(1R,2R,3R,5R)-5-Chloro-3-hydroxy-2-(8-hydroxy-oct-1-enyl)-cyclopentyl]-propyl}-thiophene-2-carboxylic acid;

5-[3-((1R,2R,3R,5R)-5-Chloro-3-hydroxy-2-pent-1-enyl-cyclopentyl)-propyl]-thiophene-2-carboxylic acid;

5-[3-((1R,2R,3R,5R)-5-Chloro-2-hept-1-enyl-3-hydroxy-cyclopentyl)-propyl]-thiophene-2-carboxylic acid;

5-[3-((1R,2R,3R,5R)-5-Chloro-2-dec-1-enyl-3-hydroxy-cyclopentyl)-propyl]-thiophene-2-carboxylic acid;

5-{3-[(1R,2R,3R,5R)-5-Chloro-3-hydroxy-2-(8-hydroxy-octyl)-cyclopentyl]-propyl}-thiophene-2-carboxylic acid;

5-{3-[(1R,2R,3R,5R)-5-Chloro-3-hydroxy-2-(7-hydroxy-heptyl)-cyclopentyl]-propyl}-thiophene-2-carboxylic acid;

5-[3-((1R,2R,3R,5R)-5-Chloro-3-hydroxy-2-oct-7-enyl-cyclopentyl)-propyl]-thiophene-2-carboxylic acid;

5-{3-[(1R,2R,3R,5R)-5-Chloro-3-hydroxy-2-(7-hydroxy-hept-1-enyl)-cyclopentyl]-propyl}-thiophene-2-carboxylic acid;

5-[3-((1R,2R,3R,5R)-5-Chloro-3-hydroxy-2-non-1-enyl-cyclopentyl)-propyl]-thiophene-2-carboxylic acid; and 5-[3-((1R,2R,3R,5R)-5-Chloro-3-hydroxy-2-decyl-cyclopentyl)-propyl]-thiophene-2-carboxylic acid.

3. An ophthalmically acceptable liquid comprising a compound according to claim 1 and an ophthalmically acceptable excipient.

* * * * *